(12) United States Patent
Koga et al.

(10) Patent No.: US 7,994,258 B2
(45) Date of Patent: Aug. 9, 2011

(54) HYPERBRANCHED POLYMER HAVING NITROXYL GROUP

(75) Inventors: Noboru Koga, Fukuoka (JP); Satoru Karasawa, Fukuoka (JP); Hiroyuki Hayashi, Fukuoka (JP); Akihiro Tanaka, Funabashi (JP); Keisuke Odoi, Chiyoda-ku (JP)

(73) Assignees: Nissan Chemical Industries, Ltd., Tokyo (JP); Kyushu University, Fukuoka-shi (JP)

( * ) Notice: Subject to any disclaimer, the term of this patent is extended or adjusted under 35 U.S.C. 154(b) by 0 days.

(21) Appl. No.: 12/739,574

(22) PCT Filed: Oct. 23, 2008

(86) PCT No.: PCT/JP2008/069236
§ 371 (c)(1),
(2), (4) Date: Jun. 1, 2010

(87) PCT Pub. No.: WO2009/054455
PCT Pub. Date: Apr. 30, 2009

(65) Prior Publication Data
US 2010/0249350 A1 Sep. 30, 2010

(30) Foreign Application Priority Data
Oct. 26, 2007 (JP) .................... 2007-279082

(51) Int. Cl.
C08F 8/30 (2006.01)
A61K 49/20 (2006.01)
H01M 4/60 (2006.01)
C08F 2/46 (2006.01)

(52) U.S. Cl. ............ 525/328.2; 525/333.4; 525/333.6; 525/356; 525/375; 522/126; 424/9.33; 429/484

(58) Field of Classification Search ........ 424/9.33; 429/484; 525/333.6, 375, 328.2, 333.4, 356; 522/126
See application file for complete search history.

(56) References Cited

U.S. PATENT DOCUMENTS
4,822,594 A 4/1989 Gibby
5,567,411 A 10/1996 Keana et al.
2003/0215390 A1* 11/2003 Rosen .................. 424/9.3

FOREIGN PATENT DOCUMENTS
JP A-2001-523215 11/2001
JP A-2004-524259 8/2004
JP A-2004-256563 9/2004
WO WO 2006/093050 A1 9/2006
WO WO 2007/136004 A1 11/2007
WO WO 2008/029688 A1 3/2008
WO WO 2008/029806 A1 3/2008

OTHER PUBLICATIONS

Ishizu, et al, Degree of Branching of Hyperbranched Polystyrenes . . . ., J. of Applied Poly. Sci., 96, 1810-1815 (2005).*
Bosman et al, Five Generations of Nitroxyl-Functionalized Dendrimers, Macromolecules, 1997, 30, 3606-3611.*
Malmstrom et al, Statistically Branched Dendritic Polymers, in Dendrimers and other Dendritic Polymers, Frechet and Tomalia (ed.), 2001, 197-208.*
International Search Report dated Dec. 2, 2008 in International Patent Application No. PCT/JP2008/069236 (with translation).
K. Ishizu et al., "Kinetics of Hyperbranched Polystyrenes by Free Radical Polymerization of Photofunctional Inimer," Macromolecules, 2002, vol. 35, No. 9, pp. 3781-3784.
K. Ishizu et al., "Synthesis of hyberbranched polymers by self-addition free radical vinyl polymerization of photo functional styrene," Macromolecular Rapid Communications, 2000, vol. 21, pp. 665-668.
K. Ishizu et al., "Novel synthesis and solution properties of hyperbranched poly(ethyl methacrylate)s by quasi-living radical copoloymerization using photofunctional inimer," Polymer International, 2004, vol. 53, pp. 259-265.

(Continued)

*Primary Examiner* — Fred M Teskin
(74) *Attorney, Agent, or Firm* — Oliff & Berridge, PLC

(57) ABSTRACT

There is provided a hyperbranched polymer having a nitroxyl group. A hyperbranched polymer comprising at least one organic radical structure (nitroxyl group) of Formula (1), Formula (2) or Formula (3):

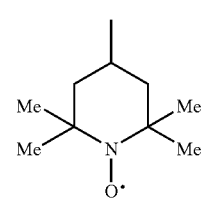

(1)

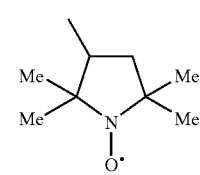

(2)

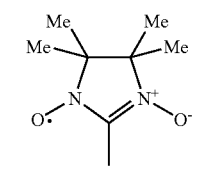

(3)

and having a weight average molecular weight measured by gel permeation chromatography in a converted molecular weight as polystyrene of 500 to 5,000,000.

7 Claims, 4 Drawing Sheets

OTHER PUBLICATIONS

G. M. Rosen et al., "Use of sodium triacetoxyborohydride in the synthesis of nitroxide biradicals," J. Chem. Soc., Perkin Trans., 2002, vol. 1, pp. 2663-2667.

H. Hayashi et al., "Design of Dendrimeric MRI Contrast Agents Having Nitronylnitroxide Cation," The Chemical Society of Japan Koen Yokoshu, 2006, vol. 86 (2), p. 1228, 3 K1-40.

H. Lee et al., "Thermally Cross-Linked Superparamagnetic Iron Oxide Nanoparticles: Synthesis and Application as a Dual Imaging Probe for Cancer in Vivo," J. Am. Chem. Soc., 2007, vol. 129, No. 42, pp. 12739-12745.

K. Ishizu et al., "Novel synthesis of branched polystyrenes by quasi-living radical copolymerization using photofunctional inimer," Polymer Internartional, 2001, vol. 50, pp. 906-910.

K. Ishizu et al., "Synthesis and characterization of hyperbranched poly(ethyl methacrylate) by quasi-living radical polymerization of photofunctional inimer," Polymer International, 2002, vol. 51, pp. 424-428.

K. Ishizu et al., "Kinetics on Formation of Hyperbranched Poly(ethyl methacrylate) via a Controlled Radical Mechanism of Photofunctional Inimer," Macromolecules, 2003, vol. 36, No. 10, pp. 3505-3510.

E. G. Rozantsev, "Free Nitroxyl Radicals; Syntheses of Some Stable Radicals and the Most Important Intermediates," Feb. 12, 1970, pp. 213-214 (XXXI).

R. C. Brasch et al., "Influence of chemical structure on nitroxyl spin label magnetic relaxation characteristics," Eur. J. Med. Chem., 1989, vol. 24, pp. 335-340.

B. Abarca-Gonzalez et al., "Synthesis, Characterisation, and Reactivity of 1-(1-Methylimidazol-2-YL)Ethenes," Synthetic Communications, 1990, vol. 20 (3), pp. 321-331.

E. Wu et al., "TEMPO-Derived Task-Specific Ionic Liquids for Oxidation of Alcohols," SYNLETT, 2005, No. 4, pp. 607-610.

H. Nishide et al., "Organic radical battery: nitroxide polymers as a cathode-active material," Electrochimica Acta, 2004, vol. 50 pp. 827-831.

* cited by examiner

[FIG. 1]
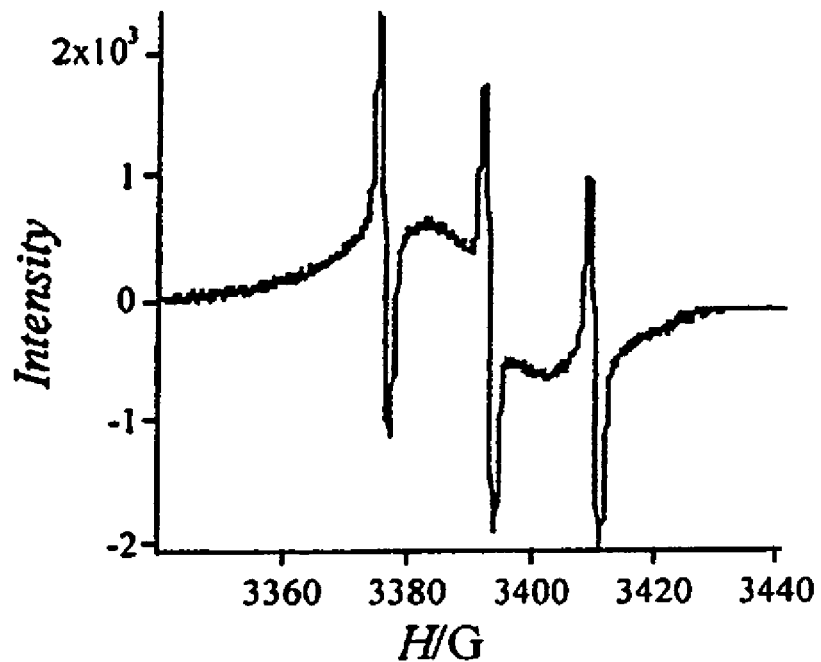
[FIG. 2]
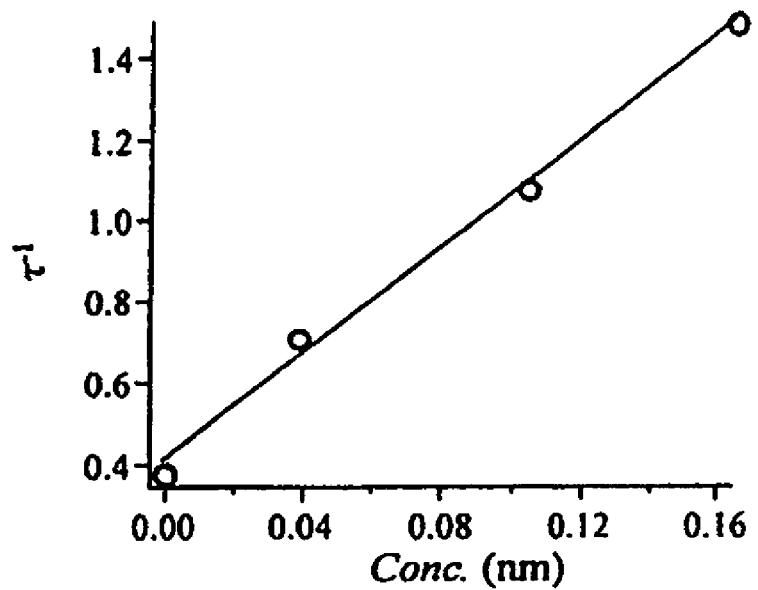

[FIG. 3]
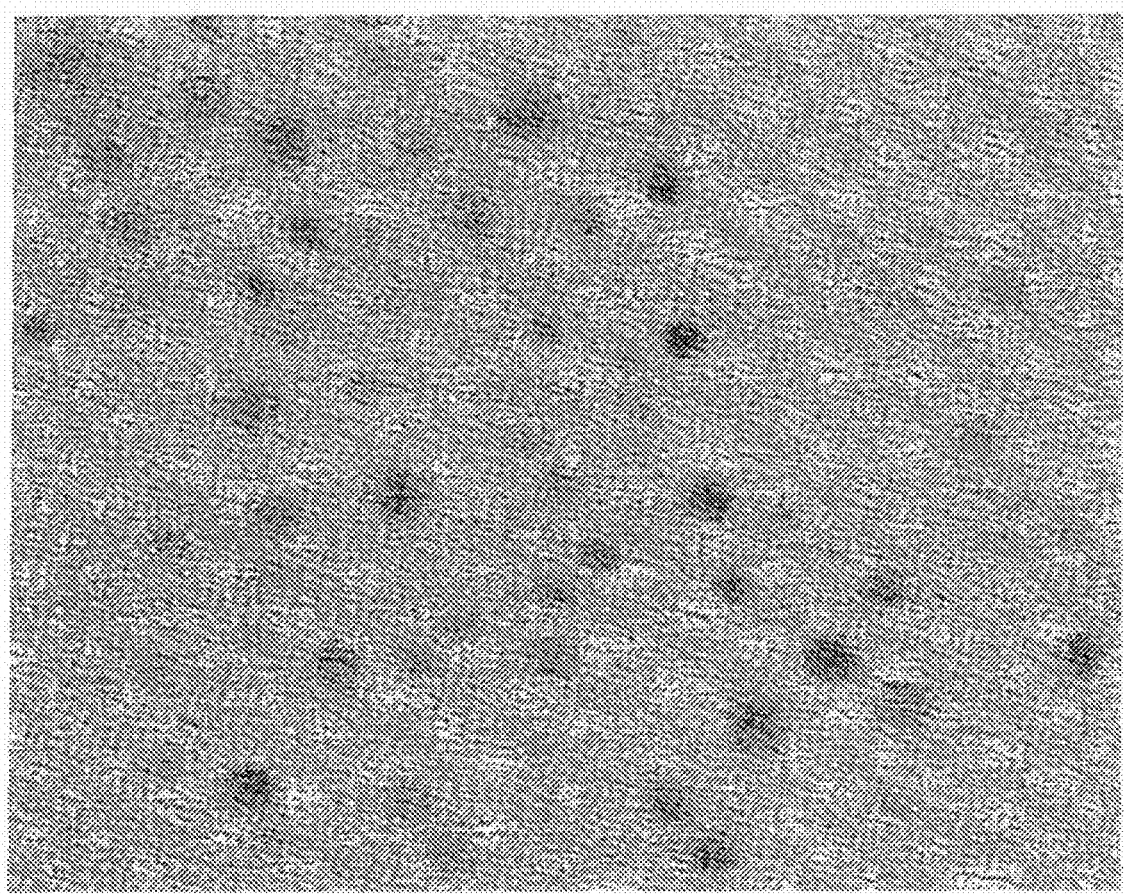

[FIG. 4]
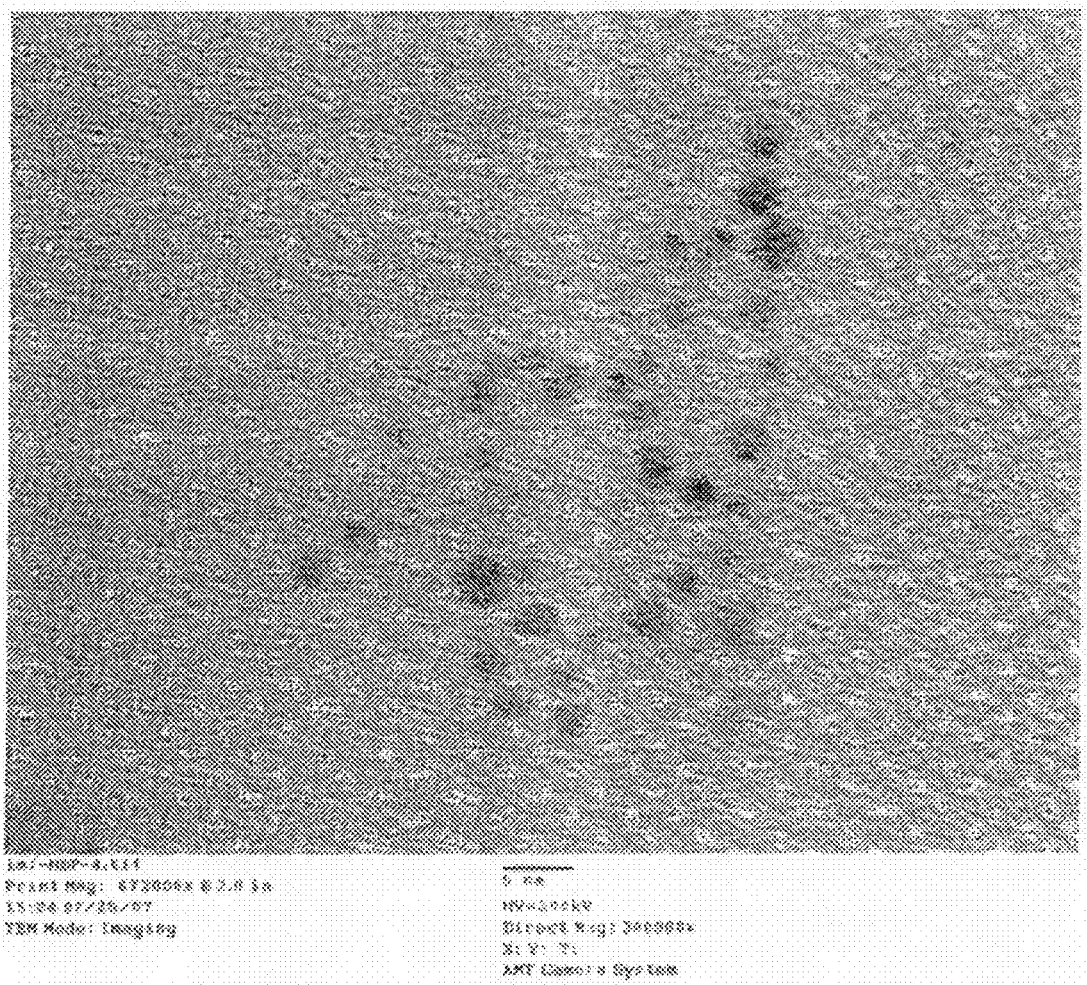
[FIG. 5]
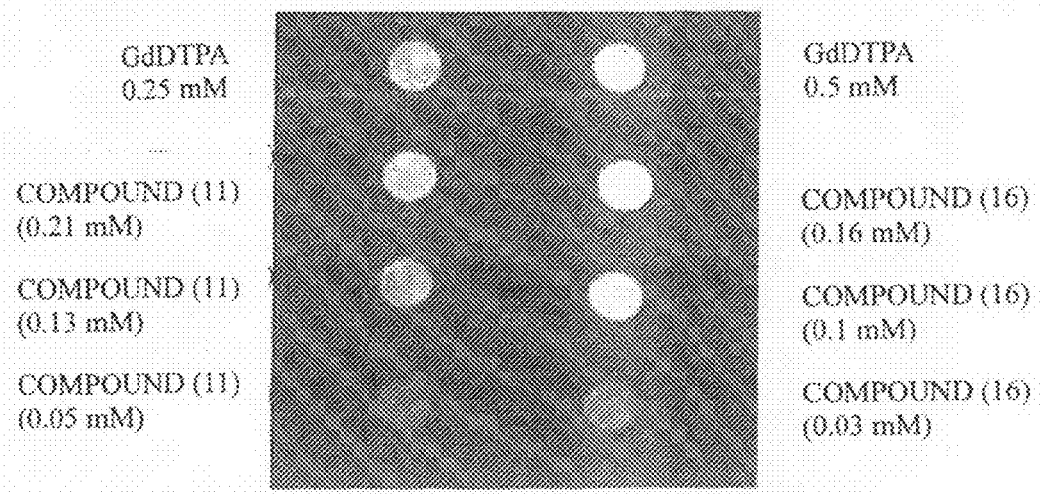

[FIG. 6]
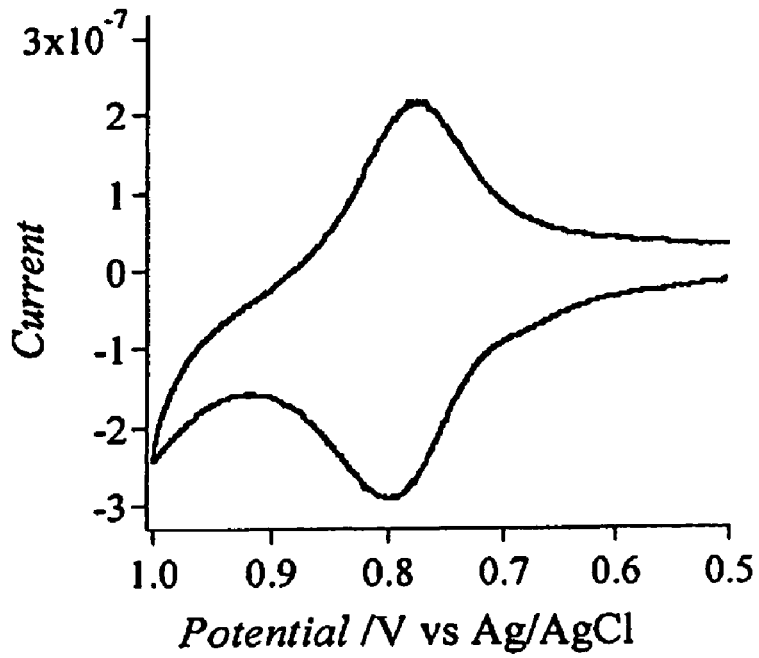
[FIG. 7]
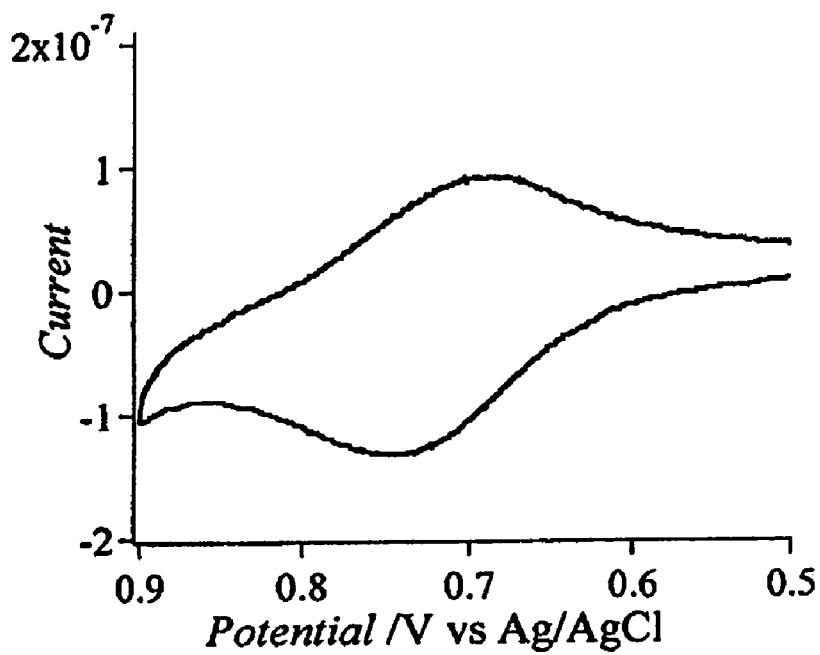

HYPERBRANCHED POLYMER HAVING NITROXYL GROUP

TECHNICAL FIELD

The present invention relates to a novel water-soluble hyperbranched polymer having an organic radical structure in the molecule thereof, and an application of the hyperbranched polymer to an MRI contrast agent.

BACKGROUND ART

A magnetic resonance imaging (MRI) method used in clinical application is a method of imaging a signal of the protons of water by which contrast between the positional information of protons existing in an organism and the surroundings is displayed two-dimensionally in a grayscale picture. The positional information is obtained by using a gradient magnetic field purposely distorting a static magnetic field in NMR and the contrast is determined by a spin density, a relaxation time, a diffusion velocity, a chemical shift, a phase and the like which are obtained as NMR information of the protons of water, lipid and the like. Particularly, the relaxation time varies according to the configuration and the movement between a water molecule containing a spin to be observed and surrounding molecules, so that the relaxation time advantageously reflects the state of a tissue and is used for diagnosis.

An MRI contrast agent in the related-art adds a contrast to between tissues having distribution quantities of water different from each other by varying the relaxation time of water in a biomedical tissue. In other words, the contrast agent is indirectly detected through a change in the relaxation time of the water protons. There are used a $T_1$ relaxation contrast agent containing Gd and Mn and a $T_2$ relaxation contrast agent using iron oxide, and by the interaction between these metal ions and the water protons, vertical and horizontal relaxations are accelerated.

However, these metal ions tend to be toxic, so that the metal ions are chelated by a ligand for reducing the ability of the biomedical tissue to absorb the metal ions. Consequently, the relaxivity possessed by the metal ions decreases and the effect as the contrast agent decreases. Then, there are disclosed a contrast agent utilizing the PRE effect (paramagnet relaxation enhancement effect) by which a metal ion enhances the relaxivity of the contrast agent by being bonded to a macromolecule (see Patent Document 1), a contrast agent having a high relaxivity by hybridizing a nitroxide compound which is an organic radical and a metal ion (see Patent Document 2), and a contrast agent having an average particle diameter of around 26 nm and having cancer cell selectivity which is produced by conjugating iron oxide nano-particles of a superparamagnet with a polymer (see Non-patent Document 1). However, all of these contrast agents contain metal ions, so that there remains a problem that the safety of the contrast agents in an organism is concerned.

Although there is disclosed a contrast agent using a dendrimer using no metal ion at all and having a nitroxyl group which is an organic radical (Patent Document 3), such a contrast agent has a problem that the relaxivity of the contrast agent is low or there is a synthetic problem for obtaining a size of the contrast agent capable of expecting the cancer cell selectivity.

Patent Document 1
  U.S. Pat. No. 4,822,594
Patent Document 2
  Japanese Translation of PCT International Application No. JP-A-2001-523215
Patent Document 3
  Japanese Translation of PCT International Application No. JP-A-2004-524259
Non-Patent Document 1
  J. Am. Chem. Soc., ASAP Article 10. 1021/ja072210i (published on web site in Sep. 25, 2007)

DISCLOSURE OF THE INVENTION

Problems to be Solved by the Invention

It is an object of the present invention to provide a novel contrast agent for MRI having an excellent water solubility, a low solution viscosity and high relaxivity and containing no metal ion.

Means for Solving the Problems

As a result of assiduous research intended to overcome these disadvantages, it has been found that there can be obtained a polymer-based MRI contrast agent having an excellent water solubility, a low solution viscosity and high relaxivity by introducing a nitroxyl group to a hyperbranched polymer terminal either directly or through a ligand, and the present invention has been completed based on the finding.

Specifically, the present invention provides, according to a first aspect, a hyperbranched polymer containing at least one organic radical structure (nitroxyl group(s)) of Formula (1), Formula (2) or Formula (3):

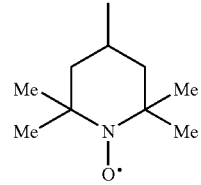

(1)

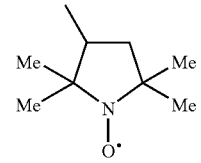

(2)

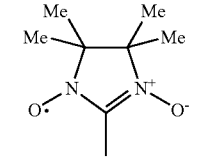

(3)

and having a weight average molecular weight measured by gel permeation chromatography in a converted molecular weight as polystyrene of 500 to 5,000,000; and according to a second aspect, the hyperbranched polymer according to the first aspect having a structure of Formula (4):

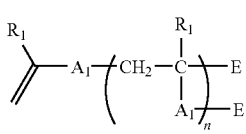
(4)

[where each $R_1$ is independently a hydrogen atom or a methyl group, each $A_1$ is independently a group of Formula (5) or Formula (6):

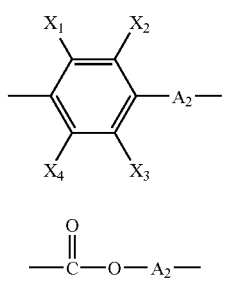
(5)

(6)

(where $A_2$ is a $C_{1-30}$ linear, branched or cyclic alkylene group which optionally contains an ether bond or an ester bond; and $X_1$, $X_2$, $X_3$ and $X_4$ are independently a hydrogen atom, a $C_{1-20}$ alkyl group, a C alkoxy group, a halogen atom, a nitro group, a hydroxyl group, an amino group, a carboxyl group or a cyano group), each E is independently a hydrogen atom, a halogen atom or a structure of Formula (7), Formula (8) or Formula (9):

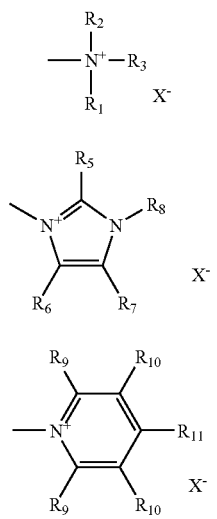
(7)

(8)

(9)

{where $X^-$ is $Cl^-$, $Br^-$, $I^-$, $PF_6^-$, $BF_4^-$ or a perfluoroalkanesulfonate; $R_2$, $R_3$, $R_4$, $R_5$, $R_6$, $R_7$, $R_9$, $R_{10}$ and $R_{11}$ are independently a hydrogen atom, a $C_{1-5}$ alkyl group, a $C_{1-5}$ hydroxylalkyl group or an organic radical structure of Formula (1), Formula (2) or Formula (3); $R_8$ is a $C_{1-5}$ alkyl group, a $C_{1-5}$ hydroxylalkyl group, a $C_{7-12}$ arylalkyl group or a group of Formula (10) or Formula (11):

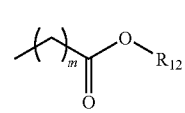
(10)

(11)

(where $R_{12}$ is an organic radical structure of Formula (1) or Formula (2); $R_{13}$ is a hydrogen atom or an organic radical structure of Formula (1) or Formula (2); $R_{14}$ is an organic radical structure of Formula (1) or Formula (2); and m is 1 to 5)}, with the proviso that at least one E has an organic radical structure of Formulae (1) to (3), and n is the number of repeating unit structures which is an integer of 2 to 100,000].

The present invention further provides, according to a third aspect, the hyperbranched polymer according to the second aspect, in which every $A_1$ is a structure of Formula (12);

(12)
—⟨benzene ring⟩—$CH_2$— according to a fourth aspect, the hyperbranched polymer according to the second aspect, in which every $A_1$ is a structure of Formula (13):

(13)
$$-\overset{O}{\underset{\|}{C}}-O-(CH_2)_l-$$

(where l is an integer of 2 to 10);

according to a fifth aspect, the hyperbranched polymer according to the third aspect, in which each E is independently a hydrogen atom, a bromine atom or a group of Formula (7) or Formula (8), where in Formula (7), $R_2$, $R_3$ and $R_4$ are independently a hydrogen atom, a methyl group or Formula (1), and in Formula (8), $R_5$, $R_6$ and $R_7$ are independently a hydrogen atom, a methyl group, Formula (1) or Formula (2) and $R_8$ is a methyl group, a benzyl group, Formula (10) or Formula (11);

according to a sixth aspect, the hyperbranched polymer according to the fifth aspect, in which at least one E is a structure of Formula (14), Formula (15), Formula (16) or Formula (17);

(14)

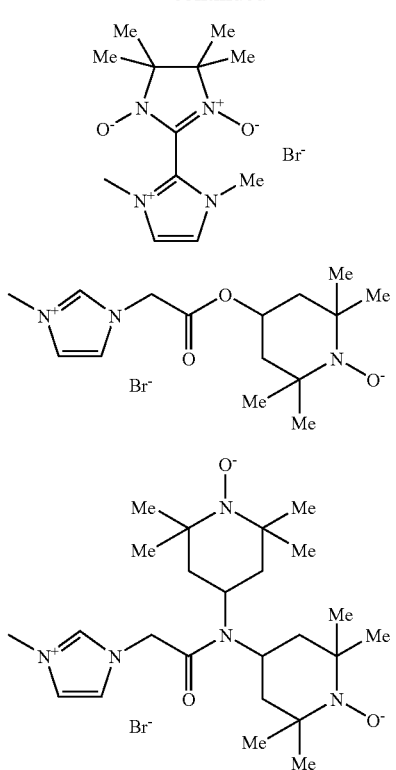

according to a seventh aspect, a contrast agent for MRI containing the hyperbranched polymer according to the first aspect; and according to an eighth aspect, an electrode activated material containing the hyperbranched polymer according to the first aspect.

Effects of the Invention

The hyperbranched polymer of the present invention contains a nitroxyl group at the molecular terminal thereof, so that the hyperbranched polymer has high relaxivity, excellent water solubility, and a low viscosity which is one of characteristics of the hyperbranched polymer. Therefore, the hyperbranched polymer of the present invention can be utilized as a novel nonmetal-type contrast agent for MRI. In addition, the hyperbranched polymer can relatively easily control its molecule weight, so that the hyperbranched polymer can provide polymers in various sizes and is expected as an innovative MRI contrast agent having a cancer cell selectivity and an organ selectivity.

The nitroxyl group supported by the hyperbranched polymer of the present invention is a stable organic radical, so that the hyperbranched polymer is expected to be applied to a secondary battery such as a radical battery and a lithium ion battery as an electrode activated material excellent in cycle properties and charging-discharging efficiency.

BEST MODES FOR CARRYING OUT THE INVENTION

Hereinafter, the embodiment of the present invention is described in detail.

The hyperbranched polymer of the present invention contains at least one organic radical structure (nitroxyl group)

and is a hyperbranched polymer having a weight average molecular weight measured by gel permeation chromatography in a converted molecular weight as polystyrene of 500 to 5,000,000. Examples thereof include the hyperbranched polymer of Formula (4). Examples of the organic radical structure supported include a structure of Formula (1), Formula (2) or Formula (3).

In Formula (4), $R_1$ is a hydrogen atom or a methyl group. In addition, $A_1$ is a structure of Formula (5) or Formula (6). n is the number of repeating unit structures which is an integer of 2 to 100,000.

In Formulae (5) and (6), $A_2$ is a linear, branched or cyclic $C_{1-30}$ alkylene group which may contain an ether bond or an ester bond; $Y_1$, $Y_2$, $Y_3$ and $Y_4$ individually are a hydrogen atom, a $C_{1-20}$ alkyl group, a $C_{1-20}$ alkoxy group, a nitro group, a hydroxyl group, an amino group, a carboxyl group or a cyano group.

Specific examples of the alkylene group of $A_2$ include: linear alkylene such as methylene, ethylene, n-propylene, n-butylene and n-hexylene; and branched alkylene such as isopropylene, isobutylene and 2-methylpropylene. In addition, examples of cyclic alkylene include a $C_{3-30}$ alicyclic aliphatic group having a monocyclic, polycyclic or crosslinked cyclic structure having 3 to 30 carbon atoms. Specific examples thereof can include a $C_4$ or more group having a monocyclo, bicyclo, tricyclo, tetracyclo, pentacyclo structure, or the like. For example, structural examples (a) to (s) of the alicyclic part in the alicyclic aliphatic group are shown as follows.

(i) 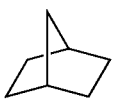

(j) 

(k) 

(l) 

(m) 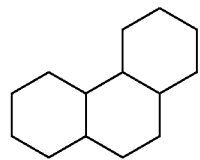

(n) 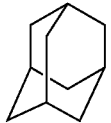

(o) 

(p)

(q)

(r) 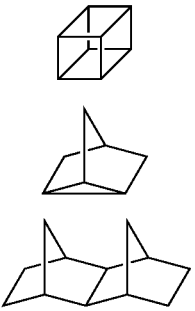

(s) 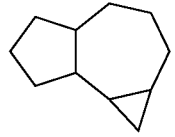

Examples of the $C_{1-20}$ alkyl group of $Y_1$, $Y_2$, $Y_3$ or $Y_4$ include a methyl group, an ethyl group, an isopropyl group, a cyclohexyl group and an n-pentyl group. Examples of the $C_{1-20}$ alkoxy group include a methoxy group, an ethoxy group, an isopropoxy group, a cyclohexyloxy group and an n-pentyloxy group. Preferred examples of $Y_1$, $Y_2$, $Y_3$ or $Y_4$ include a hydrogen atom or a $C_{1-20}$ alkyl group.

In addition, $A_1$ in Formula (4) is preferably a structure of Formula (12).

Examples of E in Formula (4) include a hydrogen atom, a halogen atom and a structure of Formula (7), Formula (8) or Formula (9). Examples of the halogen atom include a fluorine atom, a chlorine atom, a bromine atom and an iodine atom and preferred examples thereof include a bromine atom.

In Formula (7), Formula (8) and Formula (9), $X^-$ is $Cl^-$, $Br^-$, $I^-$, $PF_6^-$, $BF_4^-$ or a perfluoroalkanesulfonate and is preferably $Br^-$.

$R_2$, $R_3$, $R_4$, $R_5$, $R_6$, $R_7$, $R_9$, $R_{10}$ and $R_{11}$ are independently a hydrogen atom, a $C_{1-5}$ alkyl group, a $C_{1-5}$ hydroxylalkyl group or a structure of Formula (1), Formula (2) or Formula (3), and examples of the $C_{1-5}$ alkyl group include a methyl group, an ethyl group, an isopropyl group, a tert-butyl group, a cyclopentyl group and an n-pentyl group. Examples of the $C_{1-5}$ hydroxyalkyl group include a hydroxymethyl group, a hydroxyethyl group and a hydroxypropyl group. Preferred examples of $R_2$, $R_3$, $R_4$, $R_5$, $R_6$, $R_7$, $R_9$, $R_{10}$ and $R_{11}$ include a hydrogen atom, a methyl group and a structure of Formula (1), Formula (2) or Formula (3).

$R_8$ is a $C_{1-5}$ alkyl group, a $C_{1-5}$ hydroxylalkyl group, a $C_{7-12}$ arylalkyl group or a structure of Formula (10) or Formula (11), and examples of the $C_{1-5}$ alkyl group include a methyl group, an ethyl group, an isopropyl group, a tert-butyl group, a cyclopentyl group and an n-pentyl group. Examples of the $C_{1-5}$ hydroxyalkyl group include a hydroxymethyl group, a hydroxyethyl group and a hydroxypropyl group. Examples of the $C_{7-12}$ arylalkyl group include a benzyl group and a phenethyl group.

In Formula (10) and Formula (11), $R_{12}$ is Formula (1) or Formula (2); $R_{13}$ is a hydrogen atom, Formula (1) or Formula (2); $R_{14}$ is Formula (1) or Formula (2); and m is 1 to 5.

Next, the production method of the hyperbranched polymer having a structure of Formula (4) of the present invention is described.

The hyperbranched polymer having a structure of Formula (4) can be produced, for example according to the following scheme.

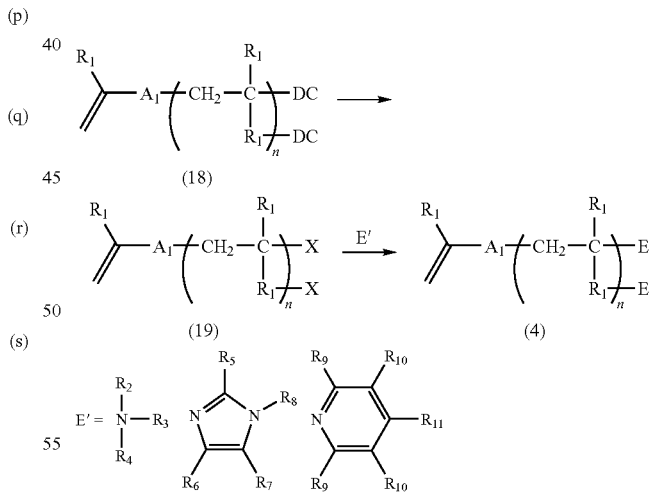

(where $A_1$, $R_1$, X, E, n, $R_2$, $R_3$, $R_4$, $R_5$, $R_6$, $R_7$, $R_8$, $R_9$, $R_{10}$ and $R_{11}$ are the same as those defined above; and DC is a dithiocarbamate group ($-SC(=S)N(R_a)R_b$ (where $R_a$ and $R_b$ individually are a $C_{1-5}$ alkyl group, a $C_{1-5}$ hydroxylalkyl group or a $C_{7-12}$ arylalkyl group, or $R_a$ and $R_b$ may be bonded to each other to form together with a nitrogen atom a ring))).

That is, by converting a hyperbranched polymer of Formula (18) having a dithiocarbamate group at the molecular terminal thereof to a hyperbranched polymer of Formula (19)

having X at the molecular terminal thereof by replacing the dithiocarbamate group of the hyperbranched polymer of Formula (18) by X and then, by reacting E', for example a tertiary amine having $R_2$, $R_3$ and $R_4$ as substituents, an imidazole having $R_5$, $R_6$, $R_7$ and $R_8$ as substituents or a pyridine having $R_9$, $R_{10}$ and $R_{11}$ as substituents which are described in the above scheme with the hyperbranched polymer of Formula (19), the hyperbranched polymer of Formula (4) can be produced.

For a reaction for synthesizing the hyperbranched polymer of Formula (19) from the hyperbranched polymer of Formula (18), a reaction condition used for replacing the dithiocarbamate group by X can be used.

For example, the reaction condition for a reaction (halogenation) when X is a halogen atom is described below.

The method of the halogenation is not particularly limited so long as the method can convert the dithiocarbamate group to a halogen atom. Examples of the halogenating agent available in the present reaction include: chlorinating agents such as chlorine, N-chlorosuccinimide, chlorinated isocyanuric acid, sulfuryl chloride, tert-butyl hypochlorite, phosphorus trichloride, phosphorus pentachloride, triphenylphosphine dichloride, copper(II) chloride and antimony pentachloride; brominating agents such as bromine, N-bromosuccinimide, N-bromoglutarimide, N,N',N"-tribromoisocyanuric acid, sodium N,N'-dibromoisocyanurate, potassium N,N-bromoisocyanurate, N,N'-dibromoisocyanuric acid, sodium N-bromoisocyanurate, N,N'-dibromohydantoin, potassium N-bromohydantoin, sodium N,N'-bromohydantoin, N-bromo-N'-methylhydantoin, 1,3-dibromo-5,5'-dimethylhydantoin, 3-bromo-5,5'-dimethylhydantoin, 3-bromo-5,5'-dimethylhydantoin, sodium 1-bromo-5,5'-dimethylhydantoin, potassium 1-bromo-5,5'-dimethylhydantoin, sodium 3-bromo-5,5'-dimethylhydantoin and potassium 3-bromo-5, 5'-dimethylhydantoin; and iodinating agents such as iodine, N-iodosuccinimide, potassium iodate, potassium periodate, periodic acid and iodic acid. It is satisfactory that the amount used of the halogenating agent is 1 to 20 times mol equivalent, preferably 1.5 to 15 times mol equivalent, and more preferably 2 to 10 times mol equivalent, based on the number of dithiocarbamate groups in the hyperbranched polymer. The conditions for the replacing reaction are accordingly selected from a reaction time of 0.01 to 100 hours and a reaction temperature of 0 to 300° C. Preferably, the reaction time is 0.1 to 10 hours and the reaction temperature is 20 to 150° C.

The reaction for replacing the dithiocarbamate group at the molecular terminal by a halogen atom is preferably effected in water or an organic solvent. The solvent to be used is preferably a solvent capable of dissolving the hyperbranched polymer having a dithiocarbamate group and the halogenating agent. In addition, when the solvent is the same solvent as that used in the production of the hyperbranched polymer having a dithiocarbamate group, the reaction operation becomes simple, which is preferred.

As the method for the halogenation, preferred is a reaction effected by heating reflux using a halogenating agent such as bromine in an organic solvent solution. The organic solvent is satisfactory so long as it does not remarkably inhibit the progression of the present reaction, and examples of the organic solvent available include: organic acid solvents such as acetic acid; aromatic hydrocarbons such as benzene, toluene, xylene, ethylbenzene and 1,2-dichlorobenzene; ether compounds such as tetrahydrofuran and diethyl ether; ketone compounds such as acetone, methyl ethyl ketone, methyl isobutyl ketone and cyclohexanone; and aliphatic hydrocarbons such as chloroform, dichloromethane, 1,2-dichloroethane, n-heptane, n-hexane and cyclohexane. These solvents may be used individually or in combination of two or more types thereof. In addition, the organic solvent is preferably used in an amount of 0.2 to 1,000 times mass, preferably 1 to 500 time(s) mass, more preferably 5 to 100 times mass, and most preferably 10 to 50 times mass, based on the mass of the hyperbranched polymer having a dithiocarbamate group at the molecular terminal thereof. In addition, in this reaction, oxygen in the reaction system is necessary to be fully purged before the initiation of the reaction and it is satisfactory to purge the inside of the system with an inert gas such as nitrogen and argon. The reaction conditions are accordingly selected from a reaction time of 0.01 to 100 hours and a reaction temperature of 0 to 200° C. Preferably, the reaction time is 0.1 to 5 hours and the reaction temperature is 20 to 150° C.

The halogenating agent remaining in the system after the completion of the reaction is desirably subjected to a decomposition treatment, and at this time, there can be used an aqueous solution of a reductant such as sodium thiosulfate and sodium sulfite or an alkaline aqueous solution such as sodium hydroxide, potassium hydroxide and calcium hydroxide. In addition, the remaining halogenating agent may be also reacted with a compound containing an unsaturated bond such as ethylene, propylene, butene and cyclohexene. The amount of such a compound used may be 0.1 to 50 equivalents, preferably 0.5 to 10 equivalents, more preferably 1 to 3 equivalent(s), based on the amount of the used halogenating agent. The hyperbranched polymer having a halogen atom at the molecular terminal thereof of the present invention obtained by the reaction as described above can be separated from the solvent in the reaction solution by the solvent removal by distillation or the solid-liquid separation. In addition, by charging the reaction solution into a poor solvent, the hyperbranched polymer having a halogen atom at the molecular terminal thereof of the present invention can be precipitated to be recovered as a powder.

Here, in the hyperbranched polymer having a halogen atom at the molecular terminal thereof of the present invention, a part of the molecular terminal may remain as a dithiocarbamate group.

The reaction for synthesizing the hyperbranched polymer of Formula (4) from the hyperbranched polymer of Formula (19) is a reaction for converting an amine compound (a tertiary amine having $R_2$, $R_3$ and $R_4$ as substituents, an imidazole having $R_5$, $R_6$, $R_7$ and $R_8$ as substituents or a pyridine having $R_9$, $R_{10}$ and $R_{11}$ as substituents) having $X^-$ as a counter ion to a quaternary amine compound.

For example, the reaction condition when X is a halogen atom is described below.

It is satisfactory that the amount used of an amine compound available in the reaction 0.1 to 20 times mol equivalent, preferably 0.5 to 10 times mol equivalent, and more preferably 1 to 5 time(s) mol equivalent, relative to 1 mol equivalent of a halogen atom in the hyperbranched polymer having a halogen atom at the molecular terminal thereof. The reaction conditions are accordingly selected from a reaction time of 0.01 to 100 hours and a reaction temperature of 0 to 300° C. Preferably, the reaction time is 0.1 to 10 hours and the reaction temperature is 20 to 150° C.

The reaction of the halogen atom at the molecular terminal with the amine compound can be effected in water or an organic solvent solution and in the presence or absence of a base. The solvent used is preferably a solvent capable of dissolving the hyperbranched polymer having a halogen atom and the amine compound. Further, when the solvent is a solvent capable of dissolving the hyperbranched polymer having a halogen atom and the amine compound, but incapable of dissolving a hyperbranched polymer having an amino group or an ammonium group at the molecular terminal thereof, the isolation of the produced hyperbranched polymer having an amino group or an ammonium group becomes easy, which is further preferred.

The organic solvent is satisfactory so long as it does not remarkably inhibit the progression of the present reaction, and examples of the solvent available include: water and organic acid solvents such as acetic acid; aromatic hydrocarbons such as benzene, toluene, xylene, ethylbenzene and 1,2-dichlorobenzene; ether compounds such as tetrahydrofuran and diethyl ether; ketone compounds such as acetone, methyl ethyl ketone, methyl isobutyl ketone and cyclohexanone; and aliphatic hydrocarbons such as chloroform, dichloromethane, 1,2-dichloroethane, n-heptane, n-hexane, cyclohexane, dimethylformamide, dimethylacetamide and N-methylpyrrolidone. These solvents may be used individually or in combination of two or more types thereof. In addition, it is preferred that the amount of the organic solvent to be used is 0.2 to 1,000 times mass, preferably 1 to 500 time(s) mass, more preferably 5 to 100 times mass, and most preferably 10 to 50 times mass, based on the mass of the hyperbranched polymer having a halogen atom at the molecular terminal thereof. In addition, in this reaction, oxygen in the reaction system is necessary to be fully removed before the initiation of the reaction and it is satisfactory to purge the inside of the reaction system with an inert gas such as nitrogen and argon. The reaction conditions are accordingly selected from a reaction time of 0.01 to 100 hours and a reaction temperature of 0 to 200° C. Preferably, the reaction time is 0.1 to 5 hours and the reaction temperature is 20 to 150° C.

Here, the hyperbranched polymer of Formula (18) having a dithiocarbamate group at the molecular terminal thereof can be synthesized according to a synthetic method by a photopolymerization of a styrene compound having a dithiocarbamate group (Koji Ishizu, Akihide Mori "Macromol. Rapid Commun. Vol. 21, p. 665 to 668 (2000)", Koji Ishizu, Akihide Mori "Polymer International Vol. 50, p. 906 to 910 (2001)", Koji Ishizu, Yoshihiro Ohta, Susumu Kawauchi "Macromolecules Vol. 35, No. 9, p. 3781 to 3784 (2002)"), or a synthetic method by a photopolymerization of an acrylic compound having a dithiocarbamate group (Koji Ishizu, Takeshi Shibuya, Akihide Mori "Polymer International Vol. 51, p. 424 to 428 (2002)", Koji Ishizu, Takeshi Shibuya, Susumu Kawauchi "Macromolecules Vol. 36, No. 10, p. 3505 to 3510 (2002)", Koji Ishizu, Takeshi Shibuya, Jaebum Park, Satoshi Uchida "Polymer International Vol. 53, p. 259 to 265 (2004)").

For example, by living radical polymerizing a dithiocarbamate compound of Formula (21) (where $R_1$, $R_a$, $R_b$ and $A_1$ are the same as those defined above), the hyperbranched polymer having a dithiocarbamate group at the molecular terminal thereof can be obtained. The hyperbranched polymer having a dithiocarbamate group at the molecular terminal thereof is considered to be generated as follows. That is, first, an $A_1$-S bond is cleaved by light irradiation or the like to the compound of Formula (21) to generate a radical species (Formula (22)). Next, the radical species of (22) is reacted with the compound of Formula (21) to generate a compound of Formula (23). Further, in Formula (23), a C—S bond or an $A_1$-S bond is cleaved to generate a radical species and the generated radical species is reacted with the compound of Formula (21) to produce a compound of Formula (24) or Formula (25). Here, in Formula (24) and Formula (25), DC is a dithiocarbamate group (—SC(=S)N($R_a$)$R_b$). Then, it is considered that from the compounds of Formula (24) and Formula (25), similar reactions are repeated and consequently, a hyperbranched polymer having a dithiocarbamate group at the molecular terminal thereof is generated.

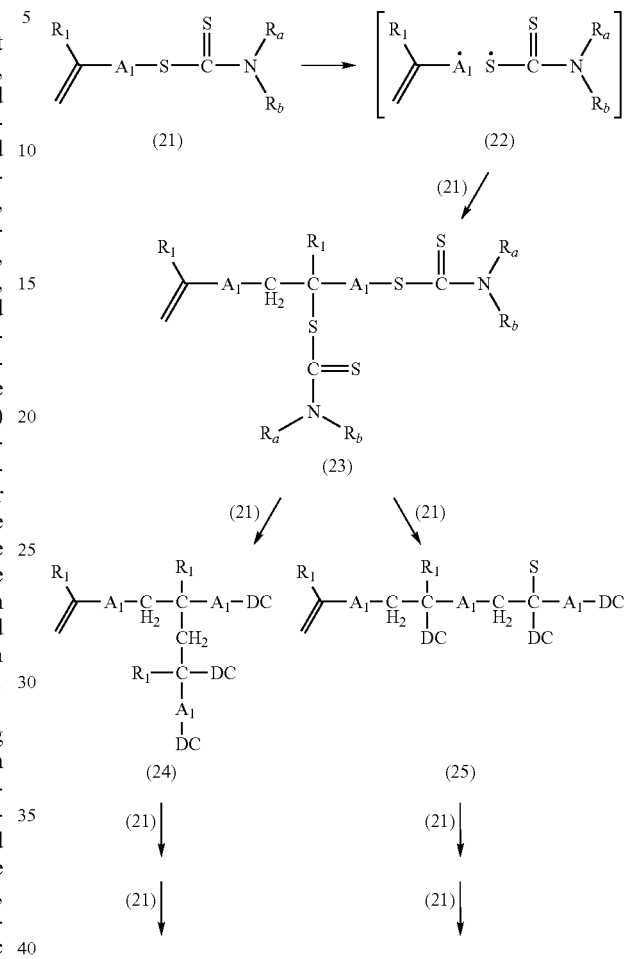

A dimethylamino TEMPO as a raw material for the introduction of a nitroxyl group can be synthesized according to "Syntheses of Some Stable Radicals p. 213 to 214 (XXXI)" and "Eur. J. Med. Vol. 24, p. 335 to 340 (1989)". In other words, by oxidizing 2,2,6,6-tetramethyl-4-piperidone with triton B to a nitroxyl derivative in the presence of sodium tungstate and by subjecting the resultant nitroxyl derivative to a reductive amination with dimethylamine and cyanoborohydride, a diethylaminoTEMPO is obtained.

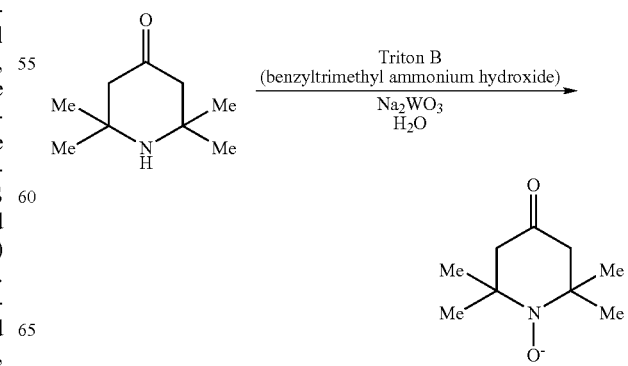

-continued

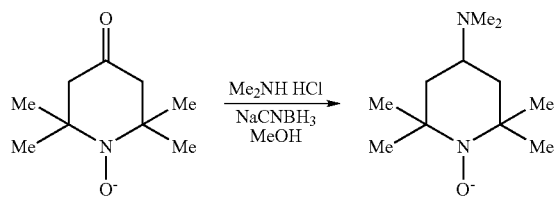

The present invention also relates to a contrast agent for MRI containing the hyperbranched polymer of the present invention.

The contrast agent for MRI containing the hyperbranched polymer of the present invention is usually used in a state in which the agent is suspended or dissolved in a solvent such as a distilled water for injection, a normal saline and a Ringer's solution and further, if necessary, the contrast agent for MRI may contain a pharmacologically acceptable additive such as a carrier and an excipient. The contrast agent for MRI containing the hyperbranched polymer of the present invention can be besides applied to the cell or the like, administered into the organism through an intravascular (intravenous, intraarterial) administration, an oral administration, an intrarectal administration, an intravaginal administration, an intra-lymphatic administration, an intraarticular administration or the like, and is preferably administered in a form of a pharmaceutical solution, an emulsion, a suspension, or the like. Although the type of the additive capable of being blended in the contrast agent for MRI containing the hyperbranched polymer of the present invention varies depending on the administration form, the administration route or the like, specifically, when the contrast agent is an injection, buffers, antibacterial agents, stabilizers, solubilizers, excipients and the like are used individually or in combination and when the contrast agent is an oral administrating agent (specifically, a pharmaceutical solution, a syrup, an emulsion, a suspension or the like), colorants, preservatives, stabilizers, suspending agents, emulsifiers, viscous drugs, sweetener, aromatic substances and the like are used individually or in combination. As the various additives, those used usually in the present field are used.

The contrast agent for MRI containing the hyperbranched polymer of the present invention can be administered for contrast imaging in substantially the same manner as that of a contrast agent for MRI in the related-art. Specific examples of the administering method include an intravenous administration and an oral administration.

In addition, the contrast agent for MRI containing the hyperbranched polymer of the present invention can be preferably used as a contrast agent besides for the human, also for various animals, and the administering form, administering route, administering dose and the like are accordingly selected according to the weight and the state of an objective animal.

The present invention also relates to an electrode activated material containing the hyperbranched polymer of the present invention.

The electrode activated material containing the hyperbranched polymer of the present invention may be used in, for example electrodes (positive electrode, negative electrode) for a lithium secondary battery, wet solar cells, sensors, fuel cells and the like.

EXAMPLES

Hereinafter, the present invention will be further described in more detail referring to Examples which should not be construed as limiting the scope of the present invention.

Reference Example 1

Synthesis of N,N-diethyldithiocarbamylmethylstyrene

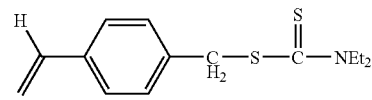

Into a 2 L reaction flask, 120 g of chloromethylstyrene (manufactured by AGC Seimi Chemical Co., Ltd.; trade name: CMS-14), 181 g of sodium N,N-diethyldithiocarbamate trihydrate (manufactured by Kanto Chemical Industry Co., Inc.) and 1,400 g of acetone were charged and the reaction was effected while stirring the resultant mixture at 40° C. for 1 hour. After the completion of the reaction, deposited sodium chloride was removed by filtering and thereafter, acetone was distilled off from the reaction solution using an evaporator to produce a reaction crude powder. The reaction crude powder was re-dissolved in toluene and the resultant toluene/water phases were separated, followed by recrystallizing the objective substance in the toluene phase in a refrigerator of −20° C. The recrystallized substance was filtered and vacuum dried to produce 206 g (yield: 97%) of the objective substance as a white powder. The purity (area percentage value) of the objective substance was measured by liquid chromatography and found to be 100%. The melting point was measured by the DSC measurement and found to be 56° C.

Reference Example 2

<Synthesis of styrene-based hyperbranched polymer (HPS) having dithiocarbamate group at molecular terminal thereof>

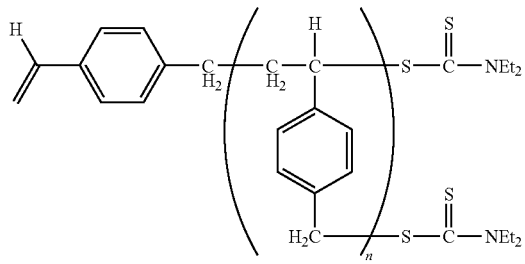

Into a 300 mL reaction flask, 108 g of N,N-diethyldithiocarbamylmethylstyrene obtained in Reference Example 1 and 72 g of toluene were charged and the resultant mixture was stirred to prepare a light yellow transparent solution, and then the inside of the reaction system was purged with nitrogen. From the center of the solution, a high pressure mercury-vapor lamp of 100 W (manufactured by Sen Lights Corporation; HL-100) was lighted to effect a photopolymerization reaction by an internal irradiation at a temperature of 30° C. for 12 hours while stirring the reaction solution. Next, the reaction solution was added to 3,000 g of methanol to reprecipitate a polymer in a massive state having high viscosity and then, supernatant fluid was removed by decantation. Further, the polymer was redissolved in 300 g of tetrahydrofuran and then, the resultant solution was added to 3,000 g of methanol to reprecipitate the polymer in a slurry state. The slurry was filtered and vacuum dried to obtain 48 g of the objective substance as a white powder. The weight average molecular weight Mw and the degree of dispersion Mw/Mn were measured by gel permeation chromatography in a converted molecular weight as polystyrene and found to be 19,000 and 3.5, respectively.

Reference Example 3

<Synthesis of styrene-based hyperbranched polymer (HPS-Br) having halogen atom at molecular terminal thereof>

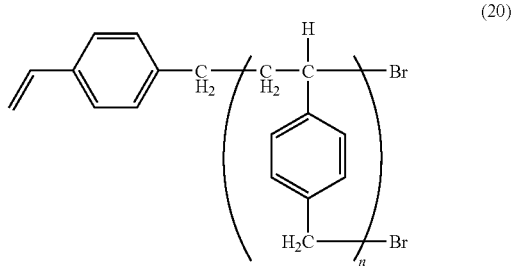

(20)

Into a 300 mL reaction flask equipped with a reflux tower, 10 g of the hyperbranched polymer having a dithiocarbamate group at the molecular terminal thereof obtained in Reference Example 2 and 50 g of chloroform were charged and the inside of the reaction system was purged with nitrogen. Into the resultant mixture, a solution in which 16.0 g of bromine (manufactured by Junsei Chemical Co., Ltd.) was dissolved in 50 g of chloroform was dropped and the resultant mixture was refluxed for 3 hours. The resultant reaction mixture was cooled down to a temperature of 30° C. and the generated orange precipitate was filtered off.

To the resultant filtrate, a saturated saline and 20% by mass sodium thiosulfate were added and the organic phase was washed. The resultant solution was dropped into 500 g of methanol to perform reprecipitation. The obtained yellow powder was dissolved one more time in 40 g of chloroform and the resultant solution was dropped into 500 g of methanol to perform reprecipitation. The obtained colorless powder was dried to produce 4.6 g of a hyperbranched polymer in which a dithiocarbamate group part of a hyperbranched polymer having a dithiocarbamate group at the molecular terminal thereof was replaced by a bromine atom. The weight average molecular weight Mw and the degree of dispersion Mw/Mn were measured by gel permeation chromatography in a converted molecular weight as polystyrene and found to be 6,600 and 2.2, respectively. The results of the element analysis were carbon: 50.2% by mass, hydrogen: 3.8% by mass, nitrogen: less than 1.0% by mass and bromine: 33.2% by mass. In the measurement result of $^1$H-NMR spectrum, it was observed that peaks at 4.0 ppm and 3.7 ppm ascribed to a methylene group of the dithiocarbamate group disappeared and a peak at 1.3 ppm ascribed to a methyl group of the dithiocarbamate group decreased. Thus, it was found to be apparent that the dithiocarbamate group at the terminal of the hyperbranched polymer obtained in Reference Example 2 was replaced by a halogen atom (bromine atom) by substantially 100%. The obtained hyperbranched polymer (HPS-Br) has a structure of Formula (20).

Example 1

Synthesis of Compound (5) (HBP-NN$^+$Br$^-$)

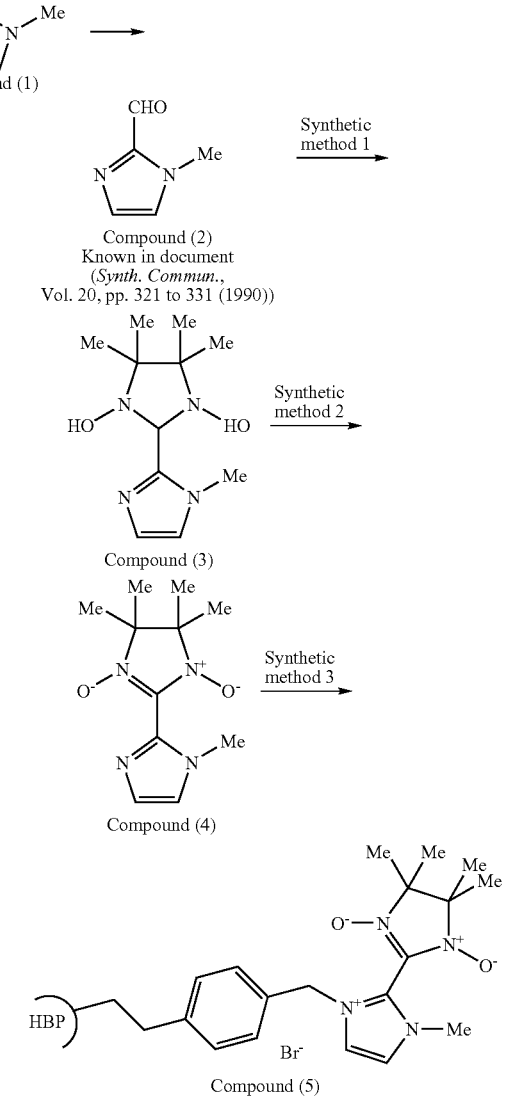

<Synthesis of Compound (2)>

According to a method in "Synth. Commun., Vol. 20, p 321 to 331 (1990)", Compound (2) was synthesized from Compound (1) (N-methylimidazole).

<Synthesis of Compound (3) (Synthetic Method 1)>

3.0 g (27.2 mmol) of Compound (2) was dissolved in 70 mL of water and to the resultant solution, 16.4 g (62.1 mmol) of 2,3-bis(hydroxylamino)-2,3-dimethylbutane sulfate monohydrate was added, followed by stirring the resultant mixture for 1 hour. The resultant reaction mixture was neutralized with sodium carbonate and was stirred further for 1 hour. The solvent was distilled off and then the resultant solid was purified by silica gel column chromatography (chloroform:methanol) to produce 4.67 g of Compound (3) as a white solid.

IR(KBr, cm$^{-1}$): 3252;
m.p. (° C.): 176 to 177° C.
$^1$H NMR (270 MHz, CDCl$_3$) δ (ppm): 7.06 (s, 1H), 6.85 (s, 1H), 5.14 (s, 1H), 3.76 (s, 1H), 1.22 (s, 6H), 1.21 (s, 6H);
FABMS (m-nitrobenzyl alcohol): 241 (M$^+$+1)
Anal. Cacld for C$_{11}$H$_{20}$H$_4$O$_2$: C, 54.98; H, 8.39; N, 23.32. Found: C, 54.85; H, 8.31; N, 23.21.

<Synthesis of Compound (4) (Synthetic Method 2)>

1.78 g (7.41 mmol) of Compound (3) was dissolved in 120 mL of methylene chloride and to the resultant solution, 10.5 g (76.1 mmol) of lead dioxide was added, followed by stirring the resultant mixture at room temperature for 1 hour. The resultant reaction mixture was filtered by sucking and from the resultant filtrate, the solvent was distilled off, followed by purifying the resultant solid by silica gel column chromatography (chloroform:methanol) to produce 1.49 g of Compound (4) as a blue solid.

IR(KBr, cm$^{-1}$): 1372;
m.p. (° C.): 155 to 157° C.
Anal. Cacld for C$_{11}$H$_{20}$N$_4$O$_2$: C, 54.98; H, 8.39; N, 23.32. Found: C, 54.85; H, 8.31; N, 23.21

<Synthesis of Compound (5) (HBP-NN$^+$Br$^-$) (Synthetic Method 3)>

39.4 mg of the hyperbranched polymer (HPS-Br) synthesized in Reference Example 3 was dissolved in 5 mL of chloroform and to the resultant solution, 71.8 mg (0.3 mmol) of Compound (4) was added, followed by heating and refluxing the resultant mixture. The resultant reaction solution was returned to room temperature and to the reaction solution, ethyl acetate was added to collect a deposited purple solid by sucking filtration. The resultant solid was vacuum dried to produce 21.5 mg of Compound (5) (HBP-NN$^+$Br$^-$).

IR(KBr, cm$^{-1}$): 3415, 2919, 2847, 1623, 1521, 1439, 1373;

Example 2

Synthesis of Compound (7) (HBP-N-TEMPO)

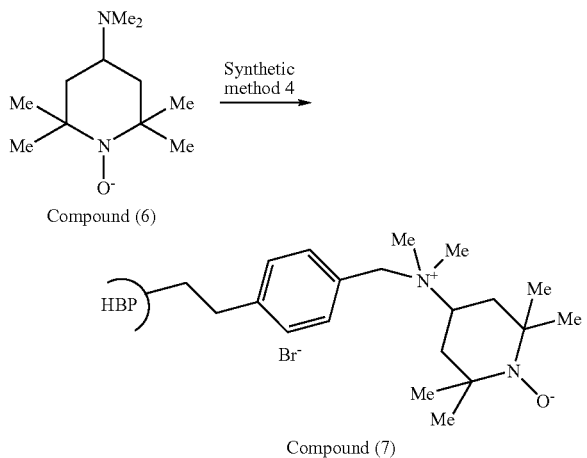

<Synthesis of Compound (6)>

According to a method in "Eur. J. Med., pp. 335 to 340 (1989)", Compound (6) (dimethylaminoTEMPO) was synthesized from 2,2,6,6-tetramethyl-4-piperidone.

<Synthesis of Compound (7) (HBP-N-Tempo) (Synthetic Method 4)>

2.5 g of the hyperbranched polymer (HPS-Br) synthesized in Reference Example 3 was dissolved in 125 mL of DMF and to the resultant solution, 5.1 g (25.4 mmol) of Compound (6) was added, followed by heating the resultant mixture at 80° C. After 8 hours of the heating, the resultant reaction solution was returned to room temperature and charged into 1,000 mL of acetone, and a deposited red solid was collected by sucking filtration. The resultant solid was vacuum dried to produce 4.0 g of Compound (7) (HBP-N-TEMPO).

IR(KBr, cm$^{-1}$): 3421, 2981, 2919, 2319, 1664;

Example 3

Synthesis of Compound (11) (HBP-Im-O-TEMPO)

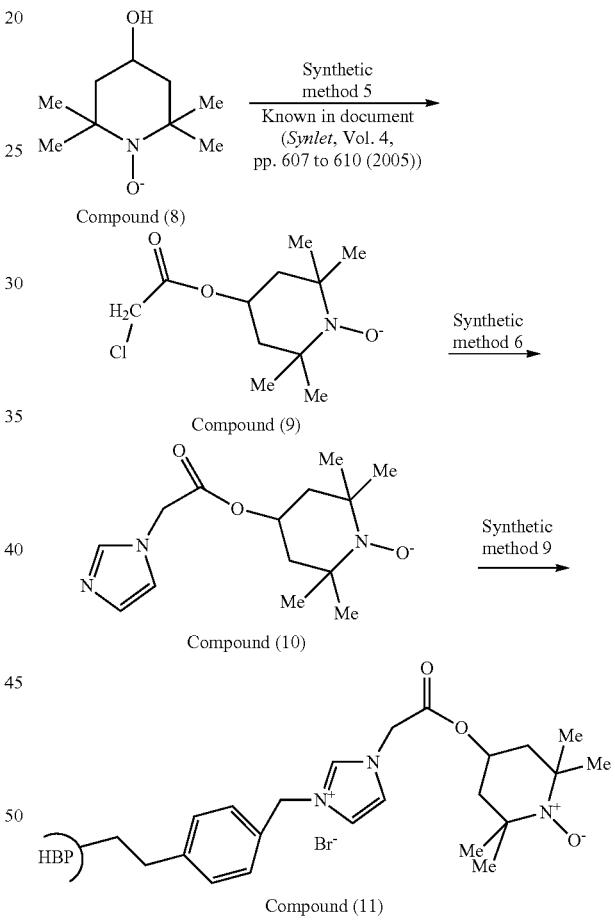

<Synthesis of Compound (9) (Synthetic Method 5)>

According to a method in "Synlet, Vol. 4, pp. 607 to 610 (2005)", Compound (9) was synthesized from Compound (8).

<Synthesis of Compound (10) (Synthetic Method 6)>

700 mg (17.5 mmol) of NaH (having 60% activity) was washed twice with n-hexane and was dried by a vacuum pump. 30 mL of dried tetrahydrofuran was added to the NaH and into the resultant mixture, a solution of 660 mg (9.7 mmol) of imidazole in 10 mL of tetrahydrofuran was dropped while maintaining the solution at 0° C. The resultant mixture was stirred for 30 minutes and then into the resultant reaction mixture, a solution of 2.0 g (8.1 mmol) of Compound (9) in 10 mL of tetrahydrofuran was dropped, followed by stirring the resultant mixture at 0° C. for 3 hours and further at room temperature for 1 hour. The resultant reaction solution was cooled in an ice bath and thereto, a diluted hydrochloric acid aqueous solution was added to neutralize the solution, followed by distilling off tetrahydrofuran and by extracting the resultant residue with methylene chloride. The resultant extract was washed with a saturated saline and then dried with magnesium sulfate, and from the resultant extract, the solvent was distilled off. The resultant residue was purified by silica gel column chromatography (ethyl acetate and then, chloroform:methanol) to produce 1.25 g of a red solid.

IR(KBr, cm$^{-1}$): 1744, 1512, 1216;

FABMS (m-nitrobenzyl alcohol): 281 (M$^{+}$+1)

Anal. Cacld for $C_{14}H_{22}N_3O_3$: C, 59.98; H, 7.91; N, 14.99. Found: C, 60.08; H, 7.74; N, 14.72.

<Synthesis of Compound (11) (HBP-Im-O-TEMPO) (Synthetic Method 9)>

400 mg of the hyperbranched polymer (HPS-Br) synthesized in Reference Example 3 was dissolved in 20 mL of DMF, and to the resultant solution, 650 mg (2.3 mmol) of Compound (10) was added, followed by heating the resultant mixture at 80° C. The reaction was effected for 6 hours and then the resultant reaction solution was returned to room temperature, followed by adding 20 mL of acetone to the reaction solution to collect a deposited red solid by sucking filtration. The resultant solid was vacuum dried to produce 910 mg of Compound (11) (HBP-Im-O-TEMPO).

IR(KBr, cm$^{-1}$): 3431, 2976, 2930, 1748, 1225, 1159;

Example 4

Synthesis of Compound (16) (HBP-Im-(TEMPO)$_2$)

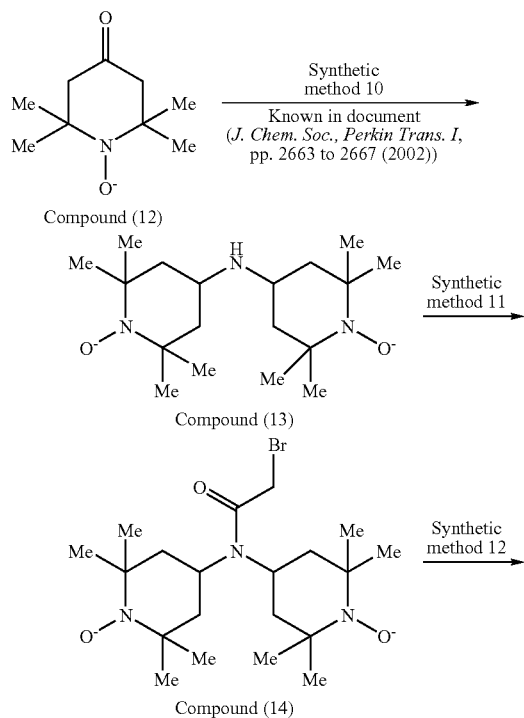

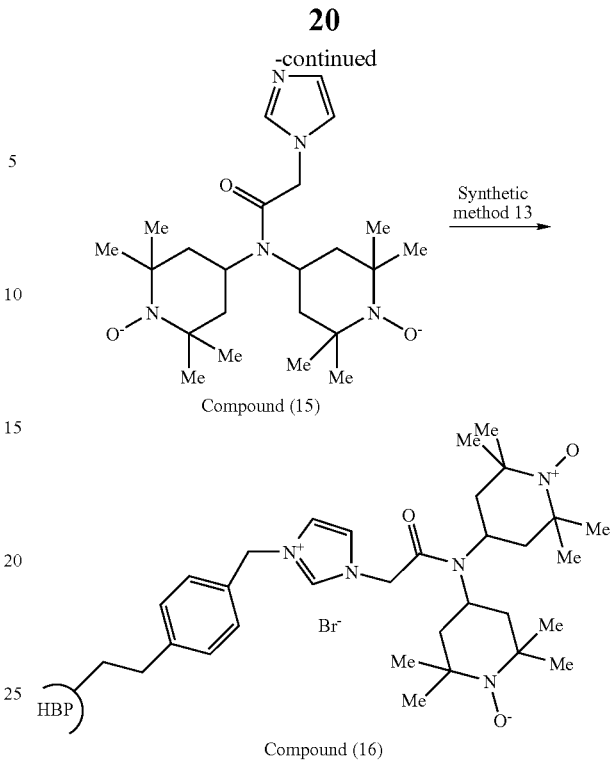

<Synthesis of Compound (13) (Synthetic Method 10)>

According to a method in "J. Chem. Soc., Perkin Trans I, pp. 2663 to 2667 (2002)", Compound (13) was synthesized from Compound (12).

<Synthesis of Compound (14) (Synthetic Method 11)>

333 mg (9.0 mmol) of NaH (having 60% activity) was washed twice with n-hexane and was dried by a vacuum pump. 15 mL of dried tetrahydrofuran and a solution of 1.5 g (4.6 mmol) of Compound (13) in 5 mL of tetrahydrofuran were dropped into the NaH while maintaining the solution at 0° C. The resultant mixture was stirred for 30 minutes, and then into the reaction mixture, 1.5 g (9.5 mmol) of bromoacetyl chloride was dropped, followed by stirring the resultant reaction mixture at room temperature for 6 hours. To the resultant reaction mixture, a diluted hydrochloric acid aqueous solution was added in an ice bath to neutralize the reaction mixture and then tetrahydrofuran was distilled off, followed by extracting the resultant residue with methylene chloride. The resultant extract was washed with a saturated saline and then dried with magnesium sulfate, and from the resultant extract, the solvent was distilled off. The resultant residue was purified by silica gel column chromatography (ethyl acetate and then, chloroform:methanol) to produce 210 mg of a red solid.

IR(KBr, cm$^{-1}$): 2973, 2931, 1651;

FABMS (m-nitrobenzyl alcohol): 447 (M$^{+}$+1)

Anal. Cacld for $C_{20}H_{36}N_3O_3Br$: C, 53.81; H, 8.13; N, 9.41. Found: C, 53.65; H, 8.14; N, 9.72.

<Synthesis of Compound (15) (Synthetic Method 12)>

20 mg (0.4 mmol) of NaH (having 60% activity) was washed twice with n-hexane and was dried by a vacuum pump. 2 mL of dried tetrahydrofuran was added to the NaH, and into the resultant mixture, a solution of 28 mg (0.4 mmol) of imidazole in 2 mL of tetrahydrofuran was dropped while maintaining the solution at 0° C. The resultant mixture was stirred for 30 minutes, and then into the reaction mixture, a solution of 150 mg (0.33 mmol) of Compound (14) in 5 mL of tetrahydrofuran was dropped, followed by stirring the resultant mixture for 3 hours and further for 1 hour at room temperature. To the resultant reaction mixture, a diluted hydrochloric acid aqueous solution was added in an ice bath to neutralize the reaction mixture and then tetrahydrofuran was distilled off, followed by extracting the resultant residue with methylene chloride. The resultant extract was washed with a saturated saline and then dried with magnesium sulfate, and from the resultant extract, the solvent was distilled off. The resultant residue was purified by silica gel column chromatography (ethyl acetate and then, chloroform:methanol) to produce 60 mg of a red solid. The solid was recrystallized in a mixed solvent of chloroform and diethyl ether to produce a red block crystal.

IR(KBr, cm$^{-1}$): 2976, 2931, 1668;
FABMS (m-nitrobenzyl alcohol): 435 (M$^+$+1)
Anal. Cacld for [$C_{23}H_{39}N_5O_3 \cdot Et_2O$]: C, 63.87; H, 9.73; N, 13.79. Found: C, 63.57; H, 9.74; N, 13.52.

<Synthesis of Compound (16) (HBP-Im-(TEMPO)$_2$ (Synthetic Method 13)>

20 mg of the hyperbranched polymer (HPS-Br) synthesized in Reference Example 3 was dissolved in 5 mL of DMF, and to the resultant solution, 70 mg (0.16 mmol) of Compound (15) was added, followed by heating the resultant mixture at 80° C. The reaction was effected for 6 hours and then the resultant reaction mixture was returned to room temperature, followed by adding 5 mL of acetone to the reaction mixture to collect a deposited red solid by sucking filtration. The resultant solid was vacuum dried to produce 70 mg of Compound (16) (HBP-Im-(TEMPO)$_2$).

IR(KBr, cm$^{-1}$): 3436, 2975, 2929, 1660;

Test Example 1

Measurement of ESR

A sample prepared by dissolving 2 mg of Compound (11) (HBP-Im-O-TEMPO) synthesized in Example 3 in 1 mL of deionized water was charged into a 1φ sample tube up to 2 cm from the bottom of the tube, and with respect to the prepared sample, ESR was measured at room temperature using EMX manufactured by Bruker BioSpin Corporation; 9.4 GHz). The graph of the measurement result is shown in FIG. 1. From the conformation of a remarkable broadening of the signal, a high-density integration of organic radicals in the hyperbranched polymer was indicated.

Test Example 2

Measurement of Relaxation Time

<Measuring Method 1>
The samples were prepared by: dissolving 1, 2, and 3 mg of each of the compounds (Compound (5), Compound (7), Compound (11), and Compound (16)) synthesized in Examples 1 to 4 in deionized water; adding deionized water to each of the resultant solutions to a volume of 0.3 mL; and charging each of the resultant solutions into a 10φ sample tube. Another sample was prepared by simply charging deionized water into a 10φ sample tube. The relaxation time (τ) of water in each of the samples was measured by an inversion recovery method using a pulse NMR apparatus (trade name: JNM-MU25RAN; manufactured by JEOL Ltd.; 0.59 T, 25 MHz, 25° C.) to determine the $T_1$ value. The inverse number of τ and the concentration were plotted on the ordinate axis and the abscissa axis respectively, and from the inclination of the plot, $r_1$ (mM$^{-1}$s$^{-1}$) was estimated.

As one example, the graph of the measurement result of Compound (11) is shown in FIG. 2.

In addition, the $r_1$ (mM$^{-1}$s$^{-1}$) values of the samples are summarized in Table 1.

<Measuring Method 2>
The relaxivity of each sample prepared in substantially the same manner as in the measuring method 1 was also measured using MRI (4.7T UNITY INOVA; manufactured by Varian, Inc.; 4.7 T, 200 MHz, 17° C.).

The $r_1$ (mM$^{-1}$s$^{-1}$) values of the samples are summarized in Table 1.

TABLE 1

| $r_1$ (mM$^{-1}$s$^{-1}$) value of each sample in measuring methods 1 and 2 | | | | |
|---|---|---|---|---|
| | Compound (5) | Compound (7) | Compound (11) | Compound (16) |
| Measuring method 1 | 3.6 | 9.1 | 7.6 | 19.9 |
| Measuring method 2 | — | 3.9 | 6.4 | 12.9 |

The concentration determining method was performed by estimating the molecular weight of a hyperbranched polymer (bromo-form) before the coupling with a radical compound as 10,000 and by assuming that 50 units of bromo group exist in one molecule of the hyperbranched polymer to estimate the molecular weight of the hyperbranched radical-coupled form. The molecular weights (Mw) of the compounds are shown as follows.

Compound (5): 21,720, Compound (7): 19,800, Compound (11): 23,850, Compound (16): 31,550

When comparing with GdDTPA (4.0 mM$^{-1}$s$^{-1}$), the compounds exhibit the same or much larger relaxivity ($r_1$) and it was shown that the weighting of $T_1$ is satisfactory.

Test Example 3

TEM (Transmission Electron Microscope) Observation

A solution in which the hyperbranched polymer (Compound (7), Compound (11)) was dissolved in THF (manufactured by Kanto Chemical Co., Inc.) so that the hyperbranched polymer has a concentration of 0.01% by weight, and was dropped into a carbon mesh grid. Then, the resultant mixture was dried to prepare a sample for the TEM observation. TEM observation (H-8000; manufactured by Hitachi, Ltd.) was performed on the sample and as a result of the observation, a particle-shaped structure having a size of around 5 nm was observed.

TEM photographs of Compound (7) and Compound (11) are shown in FIG. 3 and FIG. 4, respectively.

Test Example 4

Measurement of $T_1$-Weighted Image (Phantom Image)

A $T_1$-weighted image of an aqueous solution sample prepared using Compound (11) (Compound (16)) in substantially the same manner as that described above, was created. The relaxing rate of the water protons obtained by MRI (4.7T UNITY INOVA; manufactured by Varian, Inc.; 4.7 T, 200 MHz, 17° C.) was $T_1$-weighted and imaged by a spin echo method and a spoiled gradient echo method.

The obtained image is shown in FIG. 5.

The luminance of Compound (11) and Compound (16) is larger than that of GdDTPA in the same concentration, so that it was shown also from the image that $T_1$ is weighted to such a degree as satisfactorily clinically applicable.

Test Example 5

Measurement of Cyclic Voltammogram (CV)

0.3 mg of Compound (7) (Compound (11)) was dissolved in 1 mL of a KCl solution to prepare a sample and the sample was subjected to the measurement of cyclic voltammogram using 600B (manufactured by ALS Technology Co., Ltd.). The measurement was performed using graphite carbon as a working electrode, Ag/AgCl as a reference electrode and Pt as a counter electrode at a rate of 0.05 V/S. The graph for the measurement result of cyclic voltammogram when using Compound (7) is shown in FIG. 6, and the graph for the measurement result of cyclic voltammogram when using Compound (11) is shown in FIG. 7. In each graph, a reversible redox peak at 600 to 700 mA was confirmed and it was demonstrated that the peak corresponds to an oxidation-reduction reaction between a nitroxyl radical and an oxoammonium ion. This fact shows that Compounds (7) and (11) are effective as a material for a recyclable secondary battery.
Reference: Nishide et. al. "Electrochimica Acta, Vol. 50, pp. 827 to 831 (2004)"

BRIEF DESCRIPTION OF THE DRAWINGS

FIG. 1 is a graph showing the measurement result of ESR for Compound (11).

FIG. 2 is a graph showing the measurement result of a relaxation time for Compound (11).

FIG. 3 is a TEM photograph for Compound (7).

FIG. 4 is a TEM photograph for Compound (11).

FIG. 5 is a $T_1$-weighted image for Compound (11) and Compound (16).

FIG. 6 is a graph showing the measurement result of cyclic voltammogram when using Compound (7).

FIG. 7 is a graph showing the measurement result of cyclic voltammogram when using Compound (11).

The invention claimed is:

1. A hyperbranched polymer comprising at least one organic radical structure (nitroxyl group) of Formula (1), Formula (2) or Formula (3):

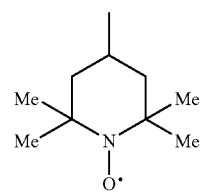

(1)

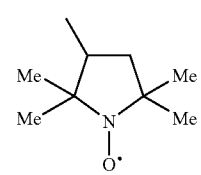

(2)

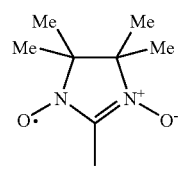

(3)

and having a weight average molecular weight measured by gel permeation chromatography in a converted molecular weight as polystyrene of 500 to 5,000,000, wherein the hyperbranched polymer has a structure of Formula (4):

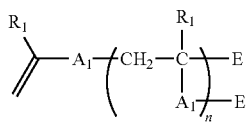

(4)

[where each $R_1$ is independently a hydrogen atom or a methyl group, each $A_1$ is independently a group of Formula (5) or Formula (6):

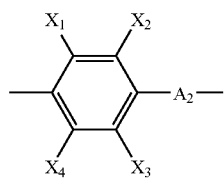

(5)

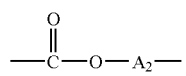

(6)

(where $A_2$ is a $C_{1-30}$ linear, branched or cyclic alkylene group which optionally contains an ether bond or an ester bond; and $X_1$, $X_2$, $X_3$ and $X_4$ are independently a hydrogen atom, a $C_{1-20}$ alkyl group, a $C_{1-20}$ alkoxy group, a halogen atom, a nitro group, a hydroxyl group, an amino group, a carboxyl group or a cyano group), each E is independently a hydrogen atom, a halogen atom or a structure of Formula (7), Formula (8) or Formula (9):

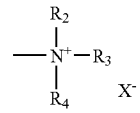

(7)

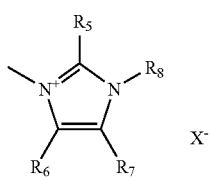

(8)

-continued

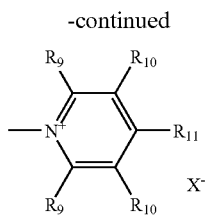
(9)

{where X⁻ is Cl⁻, Br⁻, I⁻, PF$_6^-$, BF$_4^-$ or a perfluoroalkanesulfonate; $R_2$, $R_3$, $R_4$, $R_5$, $R_6$, $R_7$, $R_8$, $R_9$, $R_{10}$ and $R_{11}$ are independently a hydrogen atom, a $C_{1-5}$ alkyl group, a $C_{1-5}$ hydroxylalkyl group or an organic radical structure of Formula (1), Formula (2) or Formula (3); $R_8$ is a $C_{1-5}$ alkyl group, a $C_{1-5}$ hydroxylalkyl group, a $C_{7-12}$ arylalkyl group or a group of Formula (10) or Formula (11):

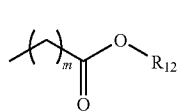
(10)

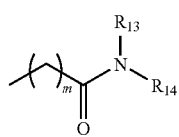
(11)

(where $R_{12}$ is an organic radical structure of Formula (1) or Formula (2); $R_{13}$ is a hydrogen atom or an organic radical structure of Formula (1) or Formula (2); $R_{14}$ is an organic radical structure of Formula (1) or Formula (2); and m is 1 to 5)}, with the proviso that at least one E has an organic radical structure of Formulae (1) to (3), and n is the number of repeating unit structures which is an integer of 2 to 100,000].

2. The hyperbranched polymer according to claim 1, wherein every $A_1$ is a structure of Formula (12):

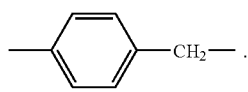
(12)

3. The hyperbranched polymer according to claim 1, wherein every $A_1$ is a structure of Formula (13):

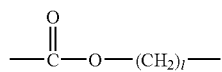
(13)

(where l is an integer of 2 to 10).

4. The hyperbranched polymer according to claim 2, wherein each E is independently a hydrogen atom, a bromine atom or a group of Formula (7) or Formula (8), where in Formula (7), $R_2$, $R_3$ and $R_4$ are independently a hydrogen atom, a methyl group or Formula (1), and in Formula (8), $R_5$, $R_6$ and $R_7$ are independently a hydrogen atom, a methyl group, Formula (1) or Formula (2) and $R_8$ is a methyl group, a benzyl group, Formula (10) or Formula (11).

5. The hyperbranched polymer according to claim 4, wherein at least one E is a structure of Formula (14), Formula (15), Formula (16) or Formula (17):

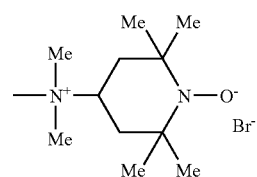
(14)

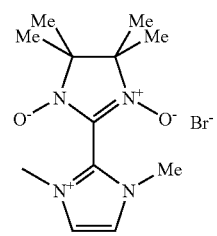
(15)

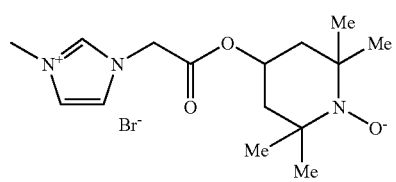
(16)

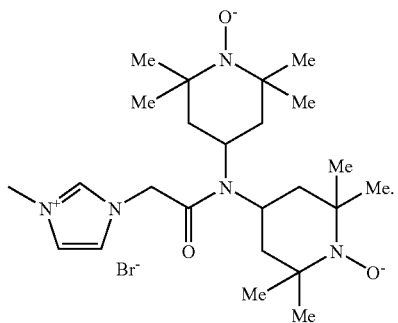
(17)

6. A contrast agent for MRI comprising the hyperbranched polymer according to claim 1.

7. An electrode activated material comprising the hyperbranched polymer according to claim 1.

* * * * *